United States Patent [19]

Ainsworth et al.

[11] Patent Number: 5,703,377
[45] Date of Patent: Dec. 30, 1997

[54] APPARATUS FOR THE INSPECTION OF CYLINDRICAL OBJECTS HAVING A BORESCOPE DEVICE

[75] Inventors: Adam Kenneth Ainsworth; Reginald Paul Glenville; Iain Alan McLean, all of Preston, United Kingdom

[73] Assignee: British Nuclear Fuels plc, Cheshire, United Kingdom

[21] Appl. No.: 576,035

[22] Filed: Dec. 21, 1995

Related U.S. Application Data

[62] Division of Ser. No. 125,641, Sep. 15, 1993, Pat. No. 5,541,418.

[30] Foreign Application Priority Data

Sep. 16, 1992 [GB] United Kingdom ............ 9219550

[51] Int. Cl.[6] .................................................. G01N 21/86
[52] U.S. Cl. ........................ 250/559.45; 250/559.46; 356/240; 356/241
[58] Field of Search .................. 250/559.45, 559.46, 250/559.22, 223 R, 227.28, 227.29; 356/376, 240, 241, 430; 382/141-143

[56] References Cited

U.S. PATENT DOCUMENTS 3,707,631 12/1972 Untermyer ............... 250/71.5 R
4,026,414 5/1977 Ellinger .................... 250/223 B
4,606,635 8/1986 Miyazawa ................. 356/240
4,849,626 7/1989 Franklin, Jr. .............. 250/227.28
4,914,289 4/1990 Nguyen .................... 250/223 B
4,930,872 6/1990 Convery ................... 356/237
5,408,104 4/1995 Gorria et al. .............. 250/559.46

FOREIGN PATENT DOCUMENTS 0 464 041  2/1992  Japan .
2 170 003  6/1986  United Kingdom .

*Primary Examiner*—Que Le
*Attorney, Agent, or Firm*—Nixon & Vanderhye P.C.

[57] ABSTRACT

Apparatus for the inspection of the end surface of a cylindrical object including a device for irradiating the end surface of the object, a detector for detecting radiation reflected by the end surface substantially parallel to the axis of the object and a calculator for calculating the proportion of the end surface which has reflected radiation directly to the detector device, wherein the means for irradiating comprises a ring source the center of the ring being substantially co-incident with the axis of the object and being substantially transparent to reflected radiation so that light reflected to the detector passes unhindered through the ring, the ring source having associated therewith a device permitting substantially uniform irradiation across the said end surface.

5 Claims, 5 Drawing Sheets

APPARATUS FOR THE INSPECTION OF CYLINDRICAL OBJECTS HAVING A BORESCOPE DEVICE

This application is a division of application of Ser. No. 08/125,641, filed Sep. 15, 1993, now U.S. Pat. No. 5,541,418.

BACKGROUND OF THE INVENTION

1. Field of the Invention

The present invention relates to the inspection of cylindrical objects, in particular the end surfaces of such objects, to detect defects on such surfaces. The objects may be nuclear fuel pellets.

2. Discussion of Prior Art

Certain cylindrical objects such as nuclear fuel pellets have to meet very demanding manufacturing quality specifications. Such objects may be manufactured by an automated manufacturing route without handling by human operators and in such a route it will be necessary to inspect the objects for surface defects using automatic apparatus. The objects may for example by sintered cylindrical oxide pellets eg $UO_2$ (uranium dioxide) pellets. The sintered pellets are inserted in stainless steel cladding tubes, the tubes being sealed to form a fuel pin and a cluster of pins being assembled to form fuel elements for use in nuclear reactor, eg a light water reactor such as a PWR or BWR type. The pellets require automatic inspection before insertion in the cladding tubes.

SUMMARY OF THE INVENTION

The purpose of the present invention is to provide an apparatus and a method for automatically inspecting the end surfaces of cylindrical objects such as nuclear fuel pellets presented to an inspection station in an automatic handling and conveying system.

In the prior art several optical techniques are known for the inspection of objects. Examples are described in GB 2104651A, GB 2057675A, EP093422A, EP 048072A, U.S. Pat. No. 5,012,117, U.S. Pat. No. 4,923,066 and U.S. Pat. No. 4,667,113. However, none of the aforementioned techniques is especially suitable for use with the end surfaces of nuclear fuel pellets, eg of the type described.

According to the present invention there is provided apparatus for the inspection of the end surface of a cylindrical object including means for irradiating the end surface of the object, detector means for detecting radiation reflected by the end surface substantially parallel to the axis of the object and calculator means for calculating the proportion of the end surface which has reflected radiation directly to the detector means, wherein the said irradiation means comprises a ring source the centre of the ring being substantially co-incident with the axis of the object and the ring being substantially transparent to reflected radiation so that radiation reflected to the detector means passes unhindered through the ring, the ring source having associated therewith means permitting substantially uniform irradiation across the said end surface.

The end surface may be flat or dished in a concave preferably circularly symmetrical fashion. The end surface may comprise a continuous surface bounded by a single edge, eg as distinct from a tubular object having an annular end with an inner and outer edge.

The said ring source may have at least one further ring source associated therewith, the ring sources all having centres substantially coincident with the said axis and being at different positions on the said axis and substantially transparent to permit radiation to be reflected to the detector means unhindered.

The principle underlying the invention is that the end surface will reflect radiation to the detector means to an extent which depends upon the texture of the surface. Where the surface is a smooth defect-free surface reflection of radiation by the surface is predominantly specular, ie close to the axis normal to the reflecting surface. Where the end surface includes a defect, eg a crack or chip, the reflection of radiation by the defect is diffuse; the intensity of radiation reflected to the detector means from the defect is low. By locating the detector means substantially on the axis of the object the detection by the detector means of low intensity specular reflection due to defects is possible.

The detector means desirably comprises an electronic imaging photo-detector; although it may alternatively comprise a non-imaging photo-detector. In the case of the non-imaging photo-detector, the output signal is proportional to the total amount of light incident on the detector, light received by the photo-detector coming substantially from the object end. In the case of the imaging photo-detector, the output signal from the detector means comprises components representing reflected radiation intensities detected by the detector means from different elements of the object surface.

In the case of the imaging photo-detector, the calculator means may comprise a signal processor which analyses the output signal provided by the detector means. Such a processor may sum all the signal components magnitudes and compare the summation with a pre-determined reference level. The calculation means may also be an image processor which analyses the output signal provided by the detector means. Such a processor may compare the output component magnitudes with a pre-determined reference level. The processor thereafter counts the number of components or pixels which have a signal magnitude (intensity, in terms of the image) respectively above and below the reference level. The number of pixels above the reference level will be representative of the area of the object that is undamaged.

In a particular form of the invention in which a succession of cylindrical objects are to be inspected in turn, the objects may be fed along a conveying track to an inspection site where they are deposited onto a support beam which is constructed so that the axis of the object (when on the support beam) projecting beyond the end surface to be inspected is inclined at an angle relative to the conveying track along which the objects previously travelled. For example, the conveying track may be horizontal and the adjacent portion of the support beam of the inspection site may be inclined so that the end surface to be inspected faces upward. In this way a light source and a detector means may be positioned on the axis without interfering with the travel of the objects.

The inspection site may be constructed so that both end surfaces of each object are inspected in turn. The apparatus may be such that one object end is inspected on a first support beam portion using a first light source and a detector means (on the axis of the object) and the other end is inspected on a second support beam portion using a second light source and detector means (on the axis of the objects).

The conveying track and the support beam may be formed of Cushion Transfer (TM) material which is described in the Applicants' UK Patent Specification No GB 2223998A the contents of which are hereby incorporated herein by reference.

The objects inspected by the apparatus and method according to the present invention may be nuclear fuel pellets. The pellets may be uranium oxide pellets for use in so-called PWR reactors. The pellets may also be fuel pellets for so-called MOX fuel in which a mixture of plutonium and uranium oxide pellets are employed.

Where the objects are MOX nuclear fuel pellets the conveyance and inspection of such pellets will take place in a radiation stable structure, eg glovebox, which protects the outside environment. In this case the space for inspection of the pellets is likely to be limited. The light source in this case may comprise a borescope device (as used in the illumination and inspection of machined holes and pipes etc) having a probe or stem with a fibre-optic ring provided at the end of the probe. The detector may comprise a miniature tv camera fitted in the borescope device at the end remote from the probe. Light for delivering to the ring via the borescope device may be passed to the borescope device by a fibre optic light guide cable. The control end processing unit for the tv camera and the light source providing light to the borescope may both be located remotely outside the radiation stable structure.

Use of a ring light source to inspect an object known from GB 2104651A. However, in that method the object is a bottle neck. Thus, the surface being inspected is not a continuous end surface enclosed by a single edge. Where a continuous end surface enclosed by a single edge such as a nuclear fuel pellet end surface is to be inspected the single ring light of GB 2194651A would be unsuitable to give substantially uniform irradiation across the inspected surface, especially where the surface is concave. By using at least two ring sources the relative positions of which can be suitable selected by adjustment or by using a borescope having an adjustable probe or stem and a fibre-optic ring provided at the end of the stem, the inspected surface can unexpectedly and beneficially be substantially uniformly irradiated. The evenness of irradiation allows a damaged surface to be distinguished from a good one by a single thresholding operation in the detection system. This avoids the need for costly high speed processors as employed in the prior art and enables popular and cheap higher resolution imaging devices to be used. In fact, a single non-imaging photo-detector may be used where the amount of received radiation, eg light, received by the photodetector is a measure of the state of the subject.

BRIEF DESCRIPTION OF THE DRAWINGS

Embodiments of the present invention will now be described by way of example with reference to the accompanying drawings, in which.

DETAILED DISCUSSION OF PREFERRED EMBODIMENTS

Figure 1:
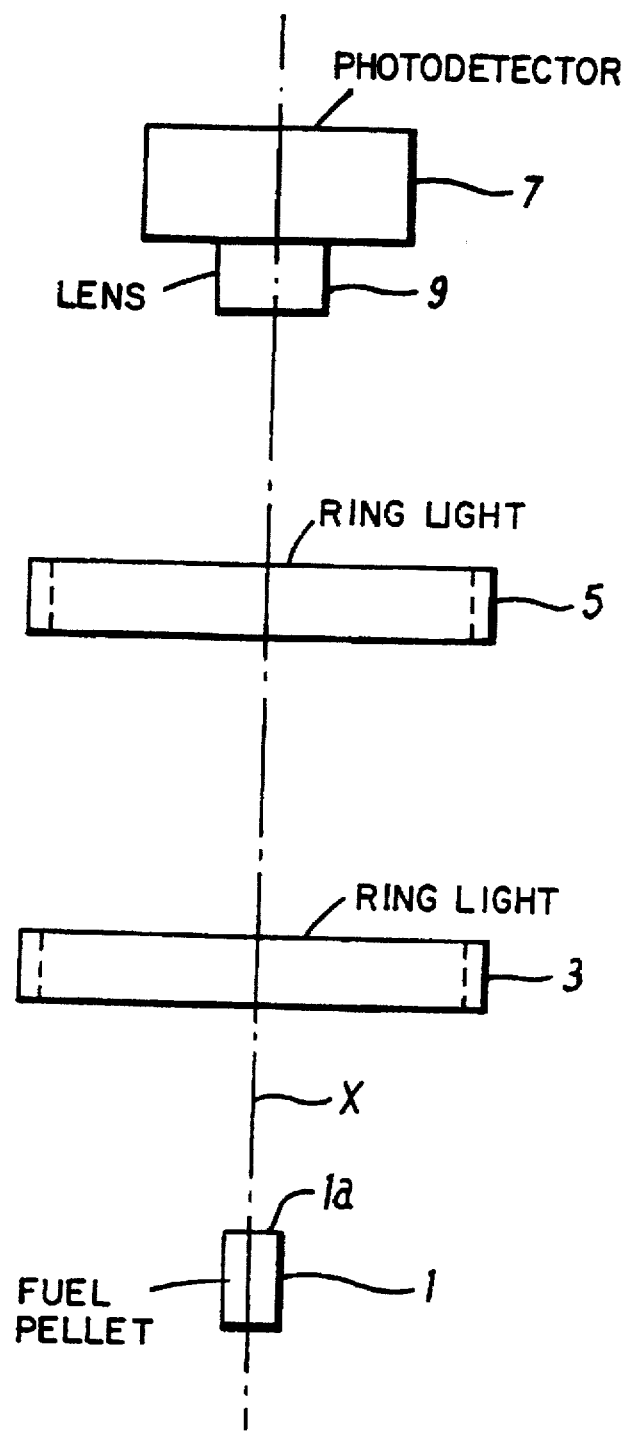
FIG. 1 is an arrangement for inspection of the end surface of a cylindrical pellet.

In FIG. 1 a cylindrical nuclear fuel pellet 1 has an end surface 1a to be inspected. The pellet 1 has an axis X shown as a broken line. Ring lights 3 and 5 (ie lights in the shape of a ring having a hollow centre) are positioned at different distances along the axis X so as to illuminate the end surface 1a. The centres of the rings of the ring lights 3, 5 both co-incide with the axis X. A photodetector 7, eg tv camera, is positioned behind the ring lights 3, 5 on the axis X. A lens 9 accompanies the photodetector 7 to focus light thereon.

Figure 2:
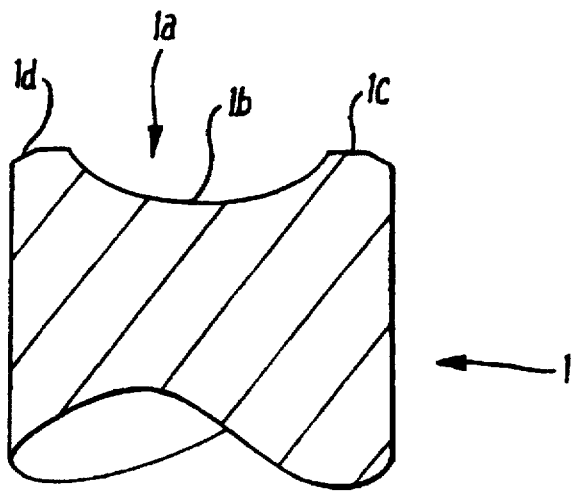
FIG. 2 is an axial cross-sectional view of a nuclear fuel pellet.

The pellet 1 shown in FIG. 1 as a simple right circular cylinder may in practice have an end surface 1a having a cross-sectional shape as shown in FIG. 2. The profile may comprise a dish 1b inside an end land area 1c, the end land area 12 having a chamfer 1d at its periphery.

Reverting to FIG. 1, the ring light 5 further from the pellet 1 illuminates the end-land area 1c and the centre portion of the dish 1b. The ring light 3 nearer the pellet illuminates the outer portion of the dish 1b and part of the chamfer 1d without adding much illumination to the area already lit by the ring light 5. More effective and repeatable measurements may be obtained by illuminating the centre portion of the dish 1b and the end-land area 1c by ring light 5 and a further ring light (not shown) beyond ring light 5. The required distances of the ring lights from the pellet 1 depend upon the surface profile of the end surface 1a or the pellet i but in practice these can be found by trial and adjustment. The effect of the adjustment is to provide substantially even illumination of the end surface 1a across its surface area.

Light from the ring lights 3, 5 is focused by the lens 9 onto the photodetector 7. The output of the photodetector 7 comprises a video signal made up of components representing an image, in terms of brightness of reflection, of component regions of the surface 1a. The components are processed in the manner described above to determine the number of pixels of the surface image having high and low reflected brightness thereby giving a measure of the area of surface 1a which incorporates any diffusely reflecting defect.

Figure 3A:
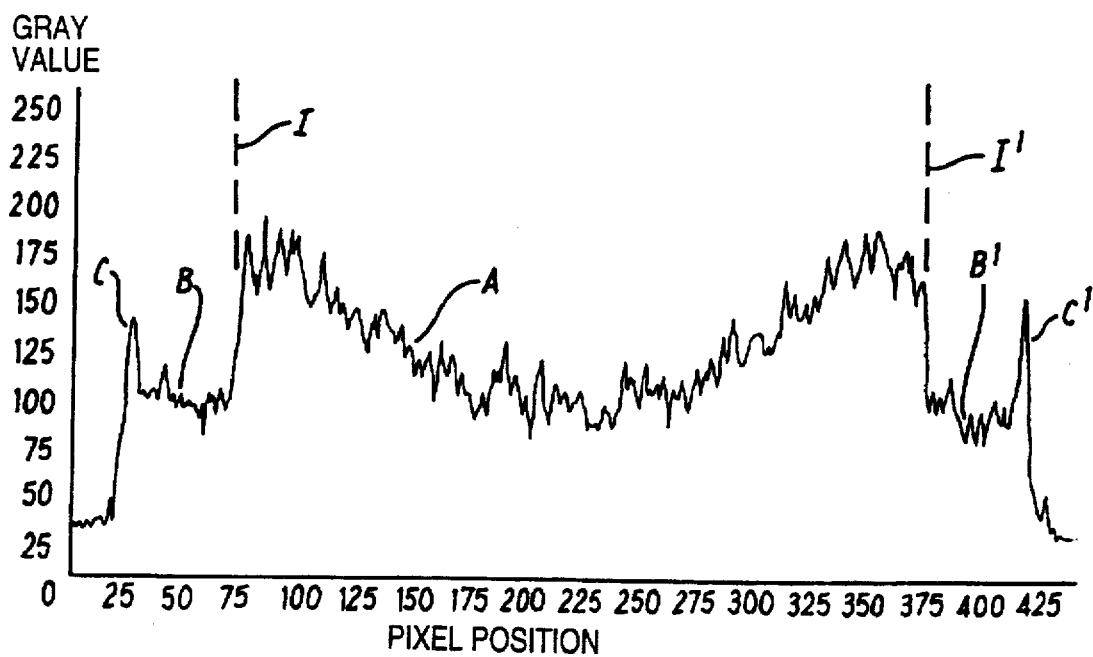
FIGS. 3a–3c are a series of three graphs showing the effect of illuminating a nuclear fuel pellet using different ring lights.
Figure 3B:
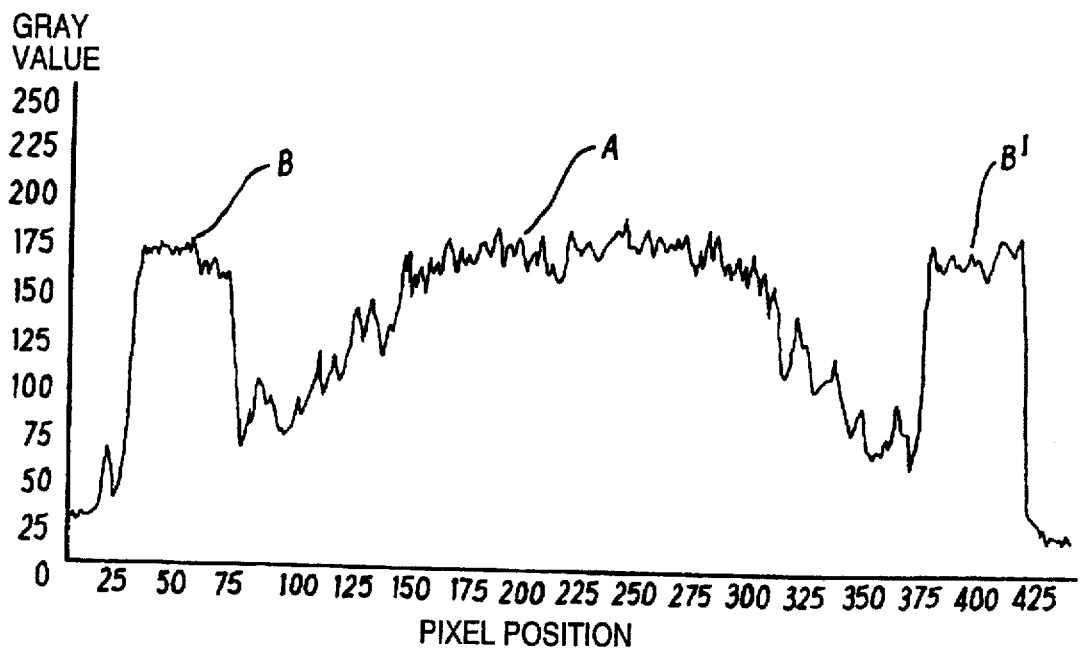

FIG. 3 shows the effect of using three ring lights to illuminate the pellet 1 of FIG. 1. The pellet illuminated in each case is defect-free. In each graph the vertical axis represents detected intensity or "gray value" of light detected at the detector 7 and the horizontal axis represents position "pixel position" across the surface of the illuminated pellet relative to an arbitary datum.

In FIG. 3(a) using only ring light 3 the light reflected from the dish 1b (see FIG. 2) of the pellet 1 produces a region A of the graph between broken lines I and I', the light reflected from the end land area 1c produces lower intensity bands B and B' end the light reflected from the chamfers 1d produces sharp peaks C and C'.

In FIG. 3 (b) which shows the effect of using ring light 5 and a further ring light beyond that but not the ring light 3, the preferential illumination of the end lands 1c and the centre of the dash 1b is illustrated by the altered shape of the regions A, B and B'.

Figure 3C:
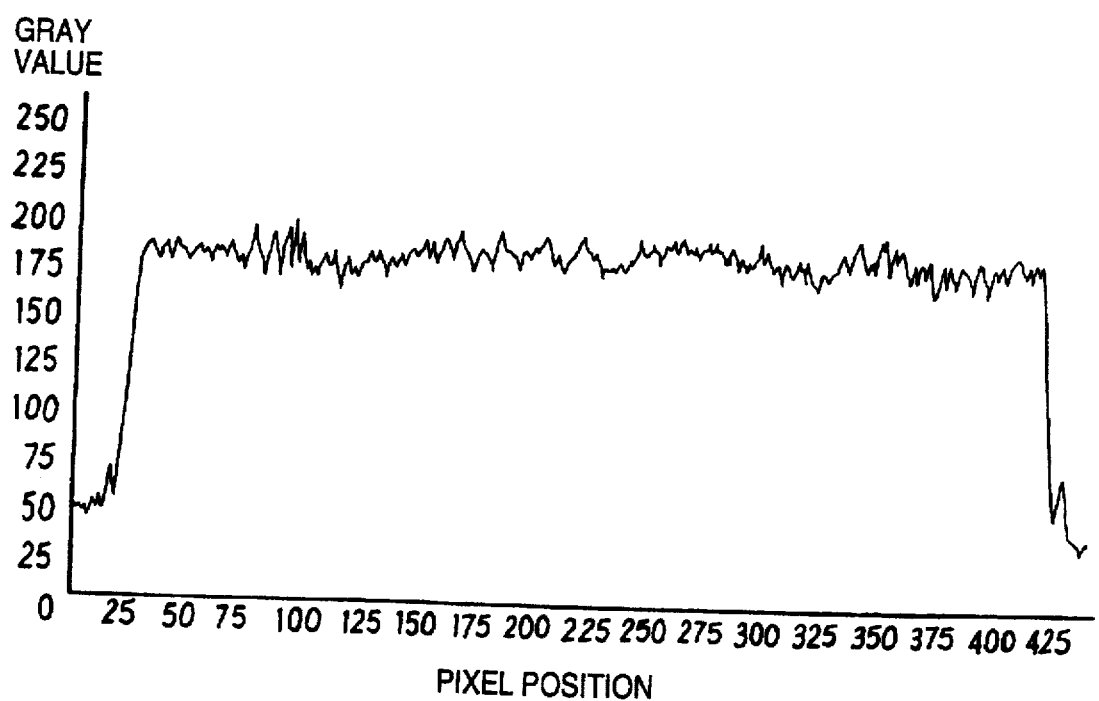

In FIG. 3(c) the effect of using all three ring lights, ie ring lights 3 and 5 and a further ring light beyond ring lights 3 and 5 is shown. In this case the illumination is substantially uniform across the end surface 1a of the pellet 1.

Use of the ring lights 3 and 5 without a further ring light gives an illumination profile similar to that shown in FIG. 3(c) except that the shape of the graph is not quite as uniform as in FIG. (c).

Figure 4:
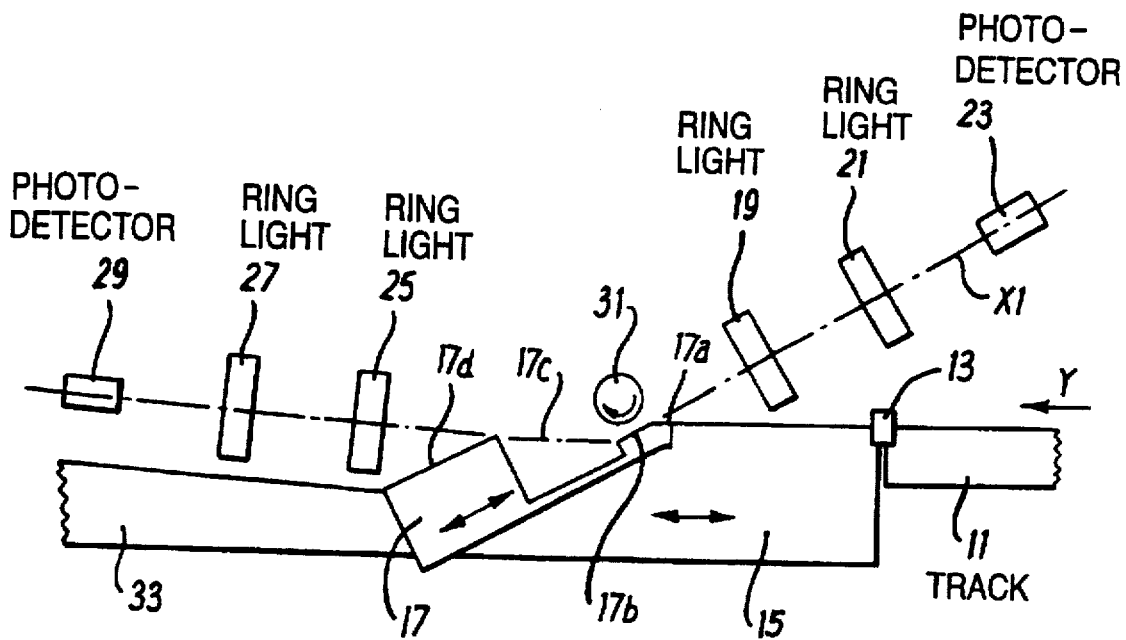
FIG. 4 is a part cross-sectional side elevation of a particular form of apparatus for carrying out inspection according to the arrangement shown in FIG. 1.

FIG. 4 shows apparatus for carrying out the inspection technique described with reference to FIG. 1 on both ends of each pellet (as in FIG. 2) in a series of pellets delivered in turn to the apparatus for inspection. Pellets (not shown) are stockpiled in a vertically walled track 11 (the walls being parallel to the direction of motion in the direction Y in the plane of the drawing). At the end of the track 11 is a feeder mechanism 13 which controls the feed rate of pellets onto a horizontal Cushion Transfer beam 15. All Cushion Transfer beams described in this example are vee-shaped beams coated with Cushion Transfer material as described in UK Patent Specification No. GB 2223998A. The angle of the vee in each beam is 90 degrees. The cylindrical pellets travel along the beams with their curved surface supported by the sides of the vee.

When a pellet is ejected from the mechanism 13 it accelerates along the beam 15 at a higher linear speed than that of transfer on the track 11. This allows pellet separation which is desirable in order to avoid pellets obscuring each other during inspection. At the end of the beam 15 the pellet is fed onto another Cushion Transfer beam 17. The beam 17 has a horizontal section 17a followed by a declined section 17b or chute followed by section 17c, which is part of the beam 15 and vibrates in a horizontal plane, followed by another declined section 17d. Inspection of the one end of the pellet takes place on the declined section 17b by ring lights 19 and 21 and a photodetector 23 all on the axis X1 of the pellet in the manner described with reference to FIG. 1. Inspection of the other end of the pellet takes place on the horizontal section 17c by ring lights 25 and 27 and a photodetector 29 all on the axis X2 of the pellet in the manner described with reference to FIG. 1.

As the pellet is tipped down the section 17b it is partially gripped by a rotating steadying wheel 31 suspended over the section 17b. The wheel 31 both slows the pellet for the instant of image capture by the photodetector 23 and ensures axial alignment of the pellet along the axis X1. The optimum position of the pellet for image capture may be sensed by a position sensor (not shown) providing an output to the photodetector 23 and the processor of the output (not shown) of the photodetector 23.

After inspection of the rear end of the pellet the pellet travels horizontally along the section 17c where its front end is inspected in a similar manner by the ring lights 25, 27 and the photodetector 29. The further declined section 17d ensures that each pellet accelerates away from the horizontal section 17c thereby avoiding obscuring the next pellet being inspected.

Finally, the pellets travel up a gradually inclined part 33 of the beam 15 to regain height lost by travelling down the inclined sections 17b and 17d. The part 33 vibrates in the horizontal plane.

Figure 5:
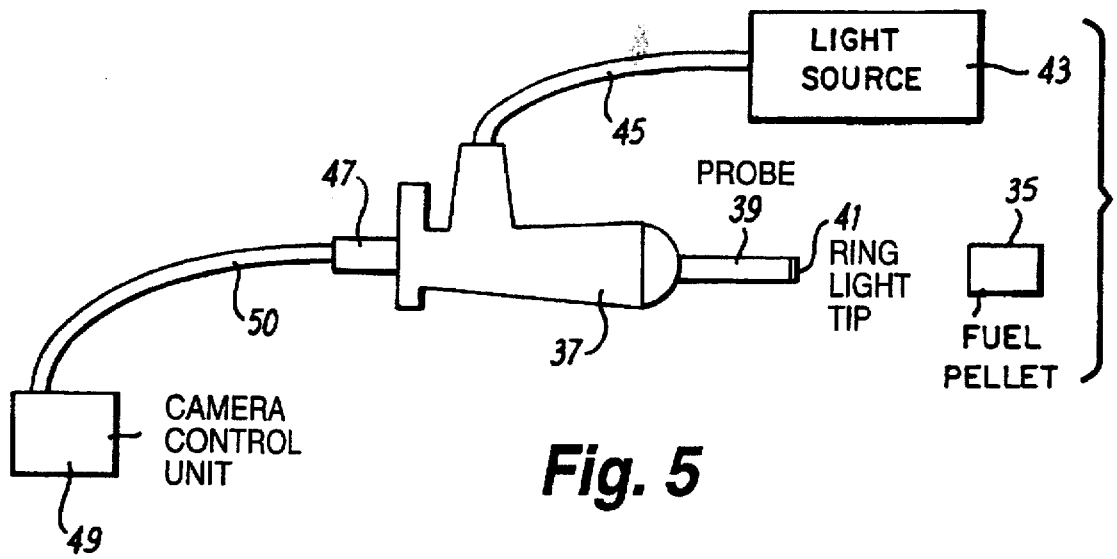
FIG. 5 is a side view of another apparatus for carrying out inspection of the end surface of a cylindrical pellet.

In the arrangement shown in FIG. 5 a MOX fuel pellet 35 is illuminated by a borescope 37 having a hollow light conducting probe 39 on the end of which is a ring light tip 41. The centre of the ring of the ring light tip 41 is coincident with the axis (not shown) of the pellet 35. Light for the ring light tip 41 is provided by a light source 43 and is fed to the borescope 37 via a light cable 45 and through the borescope 37 to the ring light tip 41. A miniature tv camera 47 is fitted in the borescope 37 at the rear end thereof. The camera 47 is controlled by a unit 49 via electrical leads in a cable 50.

The borescope 37 is adjusted in position until the light from the ring light tip 41 is focused on and evenly illuminates the end surface of the pellet 35. Light from the end surface of the pellet 35 is reflected back through the interior of the borescope 37 which is hollow and falls upon the tv camera 47. The output of the camera 47 is passed via further leads in the cable 50 to the unit 49 where it is processed by a processor (not shown).

The camera borescope 37, probe 39, tip 41 and pellet 35 are all arranged inside a glovebox. The pellet may be positioned therein by automatic handling equipment. The unit 49 and light source 43 are located outside the glovebox.

We claim:

1. Apparatus for the inspection of the end surface of a cylindrical object including means for irradiating the end surface of the object, detector means for detecting radiation reflected by the end surface substantially parallel to the axis of the object and calculator means for calculating the proportion of the end surface which has reflected radiation directly to the detector means, wherein the means for irradiating comprises a ring source the center of the ring being substantially co-incident with the axis of the object and being substantially transparent to reflected radiation so that light reflected to the detector means passes unhindered through the ring, the ring source having associated therewith means permitting substantially uniform irradiation across said end surface, wherein the means for irradiating further comprises a borescope device having a probe or stem with fiber-optic ring provided at the end of the probe.

2. Apparatus as in claim 1 wherein the detector means comprises a tv camera fitted into the borescope device at the end remote from the probe.

3. Apparatus as in claim 1 wherein in use, light for delivering to the ring via the borescope device is arranged to be passed to the borescope device by a fiber optic light guide cable, the control and processing unit for the tv camera and the light source providing light to the borescope being located remotely outside a radiation stable structure.

4. Apparatus as in claim 1 wherein the objects inspected by the apparatus are nuclear fuel pellets.

5. Apparatus as in claim 4 wherein the objects are MOX nuclear fuel pellets, the conveyance and inspection of such pellets being a radiation stable structure which protects the outside environment.

* * * * *